(12) United States Patent
Smith et al.

(10) Patent No.: US 6,551,351 B2
(45) Date of Patent: *Apr. 22, 2003

(54) SPIRAL WOUND STENT

(75) Inventors: Scott Smith, Chaska, MN (US); Brian Brown, Hanover, MN (US)

(73) Assignee: SciMed Life Systems, Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/347,066

(22) Filed: Jul. 2, 1999

(65) Prior Publication Data
US 2002/0156525 A1 Oct. 24, 2002

(51) Int. Cl.⁷ .................................. A61F 2/06
(52) U.S. Cl. ................ 623/1.16; 623/1.15; 623/1.22
(58) Field of Search .............. 623/1.15, 1.16, 623/1.2, 1.18, 1.19, 1.22

(56) References Cited

U.S. PATENT DOCUMENTS

| | | | |
|---|---|---|---|
| 5,304,200 A | 4/1994 | Spaulding | 606/198 |
| 5,549,663 A | 8/1996 | Cottone, Jr. | 623/1 |
| 5,575,816 A | 11/1996 | Rudnick et al. | 623/1 |
| 5,707,387 A | 1/1998 | Wijay | 606/194 |
| 5,716,396 A | 2/1998 | Williams, Jr. | 623/1 |
| 5,741,327 A * | 4/1998 | Frantzen | 623/1.34 |
| 5,800,456 A | 9/1998 | Maeda et al. | 606/198 |
| 5,800,515 A | 9/1998 | Nadal et al. | 623/1 |
| 5,810,872 A | 9/1998 | Kanesaka et al. | 606/198 |
| 5,824,043 A | 10/1998 | Cottone, Jr. | 623/1 |
| 5,833,699 A | 11/1998 | Chuter | 606/198 |
| 5,913,897 A | 6/1999 | Corso, Jr. et al. | 623/1 |
| 5,922,020 A * | 7/1999 | Klein et al. | 606/194 X |
| 5,925,061 A * | 7/1999 | Ogi et al. | 623/1.2 |
| 5,938,697 A * | 8/1999 | Killion et al. | 623/1.15 |
| 6,132,461 A * | 10/2000 | Thompson | 623/1.15 |

FOREIGN PATENT DOCUMENTS

| | | |
|---|---|---|
| DE | 29816878 U | 2/1999 |
| EP | 0 312 852 A1 | 4/1989 |
| EP | 0 870 483 A2 | 10/1998 |
| WO | 95/26695 | 10/1995 |
| WO | 96/26689 | 9/1996 |
| WO | 97/14375 | 4/1997 |
| WO | 99/43272 | 9/1999 |

* cited by examiner

Primary Examiner—Bruce Snow
Assistant Examiner—Brian E Pellegrino
(74) Attorney, Agent, or Firm—Vidas, Arrett & Steinkraus P.A.

(57) ABSTRACT

A self-expanding tubular stent comprises a plurality of stent segments. Each stent segment is formed of an elongate ribbon having portions cut therefrom to form a wave-like undulating pattern, opposed edges of which are attached to one another so as to form a generally cylindrical configuration. A disclosed method effects formation of such an expandable tubular stent by first providing an elongate flat ribbon of biocompatible stent material and selectively removing portions of such material to form an undulating wave-like pattern along the length of the ribbon. The ribbon is then coiled into a generally cylindrical configuration and opposed ends of the ribbon are secured to one another to form a generally cylindrical and expandable spiral stent section. After forming a plurality of such stent sections, the stent sections are arranged in longitudinal succession and interconnected so as to form an elongated stent configuration.

25 Claims, 3 Drawing Sheets

SPIRAL WOUND STENT

FIELD OF THE INVENTION

This invention relates generally to a method of constructing an expandable tubular stent from a flat wire or ribbon. More particularly, the present invention is directed to such a stent formed from an elongate ribbon having portions cut therefrom where the cut ribbon is wound into a cylindrical stent configuration.

BACKGROUND OF THE INVENTION

It is well known to employ various endoprostheses for the treatment of diseases of various body vessels. One type of endoprosthesis is commonly referred to as a stent. A stent is a generally longitudinal tubular device formed of biocompatible material which is useful in the treatment of stenosis, strictures or aneurysms in body vessels such as blood vessels. These devices are implanted within the vessel to reinforce collapsing, partially occluded, weakened or abnormally dilated sections of the vessel. Stents are typically employed after angioplasty of a blood vessel to prevent re-stenosis of the diseased vessel. While stents are most notably used in blood vessels, stents may also be implanted in other body vessels such as the urogenital tract and bile duct.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern. Examples of various stent configurations are shown in U.S. Pat. Nos. 4,503,569 to Dotter; U.S. Pat. No. 4,733,665 to Palmaz; U.S. Pat. No. 4,856,561 to Hillstead; U.S. Pat. No. 4,580,568 to Gianturco; U.S. Pat. No. 4,732,152 to Wallsten and U.S. Pat. No. 4,886,062 to Wiktor.

Flexibility is a particularly desirable feature in stent construction as it allows the stent to conform to bends in a vessel. Many of the stent configurations presently available are formed of a plurality of aligned, expandable, relatively inflexible, circular segments which are interconnected by flexible elements to form a generally tubular body which is capable of a limited degree of articulation or bending. It has been found, however, that certain stents promote binding, overlapping or interference between adjacent segments on the inside of a bend due to movement of the segments toward each other and into contact. Also, on the outside of a bend, segments can move away from each other, leaving large gaps, leading to improper vessel support, vessel trauma, flow disturbance, kinking, balloon burst during expansion and difficult recross for devices to be installed through already implanted devices and to unsupported regions of the vessel.

Accordingly, it is desirable to provide an expandable tubular stent which exhibits sufficient radial strength to permit the stent to maintain patency in an occluded vessel and yet be capable of elongation by affixing multiple stent segments thereto. The present invention prevents reoccurrence of occlusions in a passageway and prevents recoil of a vessel wall by providing an expandable tubular stent of generally open, cylindrical configuration that utilizes reduced thickness struts. Such a stent prevents recoil of body passageway walls and allows elongation of the stent to prevent migration of the stent within a luminal structure.

SUMMARY OF THE INVENTION

It is an object of the present invention to provide an improved intraluminal prosthetic device that will hold open an occluded, weakened or damaged vessel.

It is a further object of the present invention to provide a spiral wound stent capable of self-expansion within a vessel into which it is implanted.

It is still a further object of the present invention to provide a longitudinally flexible stent of open configuration that exhibits improved radial and longitudinal flexibility in both the stent body segments and in the flexible joints between the segments.

It is yet another object of the present invention to provide a method of forming such a longitudinally flexible stent from a flat wire or ribbon of biocompatible material which is cut and spirally wound over a cylinder to form a tubular stent.

It is still another object of the present invention to form at least one connector on each such stent and attach each connector so as to form a longitudinal succession of stent segments.

In the efficient attainment of these and other objectives, the present invention provides a self-expanding tubular stent comprising a plurality of stent segments. Each stent segment is formed of an elongate ribbon having portions cut therefrom to form a wave-like undulating pattern, opposed edges of which are attached to one another so as to form a generally cylindrical configuration. A disclosed method effects formation of such an expandable tubular stent by first providing an elongate flat ribbon of biocompatible stent material and selectively removing portions of such material to form an undulating wave-like pattern along the length of the ribbon. The ribbon is then wound into a generally cylindrical configuration, and opposed ends of the ribbon are secured to one another to form a generally cylindrical and expandable spiral stent section. After forming a plurality of such stent sections, the stent sections are arranged in longitudinal succession and interconnected so as to form an elongated stent configuration.

DETAILED DESCRIPTION OF THE PREFERRED EMBODIMENTS

The present invention is a multiple-segment slotted tube which is particularly suited for use as an endoprosthesis. In particular, a flat ribbon or wire comprised of biocompatible material is provided wherein the ribbon has predetermined length, width and thickness. A stent is formed from this material by forming cuts in the material so that the cut material can be stretched to form an undulating wave-like pattern. The cut ribbon is then spirally wound into a generally cylindrical shape to form a stent segment. Plural stent segments can be affixed to one another in longitudinal succession to form an elongate stent using a connector which is formed from the ribbon. Interconnection between adjacent stent segments is achieved by combining two connectors where the connectors may be fabricated at one-half their original width and bonded together by welding or other means.

Figure 1:
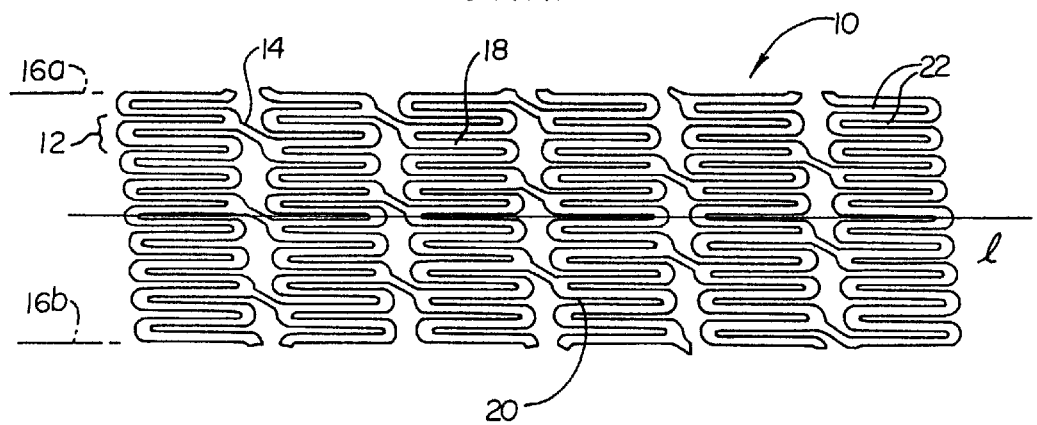
FIG. 1 shows a plan view of an expandable tubular stent of the prior art.

Now referring to the drawings wherein like elements are identically numbered, FIG. 1 shows an elongated tubular stent of the prior art as disclosed in commonly assigned International Application No. PCT/US96/02615 to Brown et al., which is incorporated by reference herein. Brown discloses a segmented articulatable stent 10 of open structure, comprised of a plurality of parallel struts 12 aligned on a common longitudinal axis 1 having annular connectors 14 disposed therebetween. Stent 10 has opposed edges 16a and 16b which, when connected, define a central lumen of a generally tubular stent body. The body therebetween of stent 10 defines an interior surface 18 and an exposed exterior surface 20. The stent is formed to have a generally open configuration having a plurality of passages or openings 22 therethrough. These openings provide for longitudinal flexibility of the stent as well as to permit the stent to be radially expanded once deployed in a body lumen such as a blood vessel.

From a manufacturing perspective, this stent provides satisfactory performance, yet is relatively difficult and costly to construct. As cutting of the stent configuration is commonly performed after the stent material has been placed into its tubular configuration, cutting of a complex pattern into the tube is difficult to achieve. For example, a type of cutting method known as etching involves difficult processing techniques which require state-of-the-art cutting machinery and costly supervision of the cutting process. If etching is conducted on a tubular article, extra resources must be expended for supervision and quality assurance of the preferred stent design. Thus, it is desirable to retain the performance advantages of the current stent design while improving the methods of manufacture thereof.

The present invention provides an improved method of forming a stent 10 of the type shown in FIG. 1.

Figure 2:
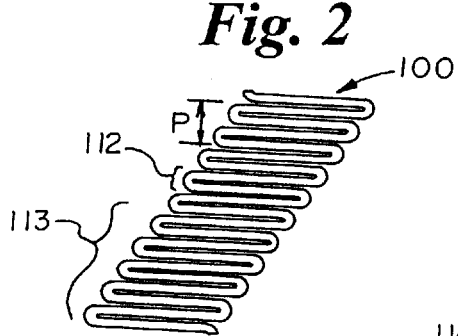
FIG. 2 shows an expandable spiral wound stent segment of the present invention.
Figure 2A:
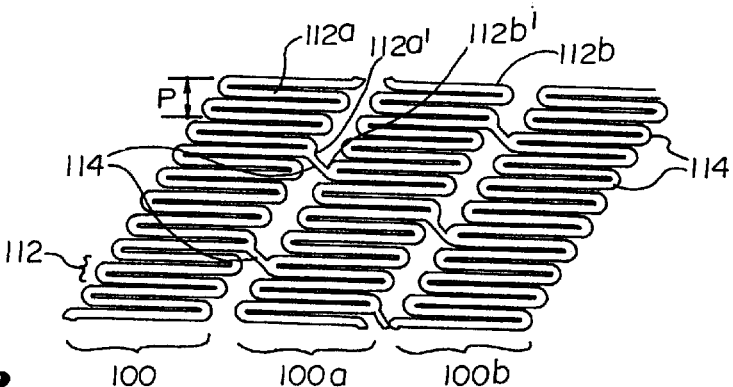
FIG. 2A shows an elongated stent utilizing plural expandable stent segments of FIG. 2.

Referring to FIG. 2, a single stent segment 100 of configuration similar to that shown in FIG. 1 is shown. Stent segment 100 includes a plurality of struts 112 which undulate in a wavelike pattern 113 having period P. While stent segment 100 may be employed as a stent in certain situations, more commonly to achieve enhanced kink resistance and flexibility, multiple stent segments 100 may be affixed to one another to form an elongated stent 100' as shown in FIG. 2A. Upon expansion, stet segment 100 reveals a repeating pattern of waves that are distributed in a spiral-like fashion about an axis 1. Although the spiral is shown in a pattern descending from right to left, the spiral may be alternately oriented to descend left to right.

Referring now to FIGS. 3 and 3A–3E, a preferred method of forming stent segment 100 may now be described. Stent 100 is formed from an elongate ribbon 200 which may a biocompatible stent material of the type typically used in the formation of conventional stems. The present invention is applicable to self-expanding stent configurations as well as mechanically expandable configurations; therefore, the material composition of the ribbon may be chosen from a wide variety of well-known and utilized stent materials. For example, the stent may be made from stainless steel, titanium, platinum, gold and other biocompatible materials. Thermoplastic materials which are inert in the body may also be employed. However, the stent is preferably formed from a temperature-sensitive memory alloy which changes shape at a designated temperature or temperature range. Shape memory alloys having superelastic properties generally made from specific ratios of nickel and titanium, commonly known as Nitinol, are among the preferred stent materials.

Figure 3:
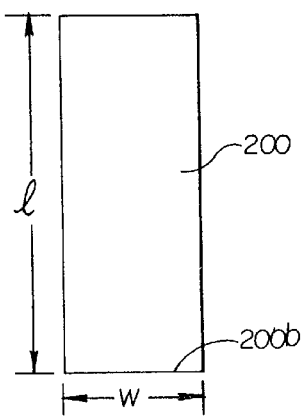
FIG. 3 shows a plan view of a piece of flat ribbon-like stent material used to form the spiral wound stent of the present invention.
Figure 3A:
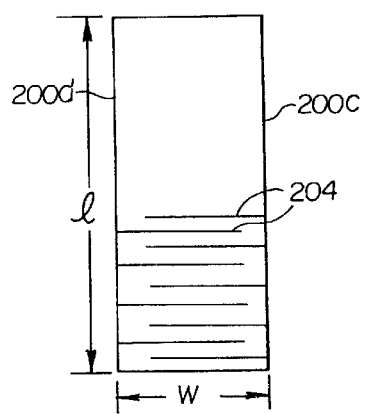
FIG. 3A shows a plan view of the flat material of FIG. 3 having lateral slits cut or etched therethrough.

As shown in FIG. 3A, ribbon 200 is of predetermined length l, width w and thickness corresponding to the desired parameters and performance of a generally cylindrical stent to be formed therefrom. Ribbon 200 also has opposing transverse edges 200a and 200b which, as will be described below in further detail, may be affixed to one another after further fabrication to form a generally cylindrical shape.

Figure 3B:
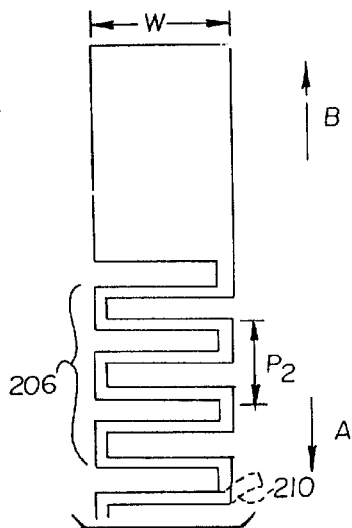
FIG. 3B shows a plan view of the cut material of FIG. 3A after stretching thereof to define a wavelike formation.
Figure 3C:
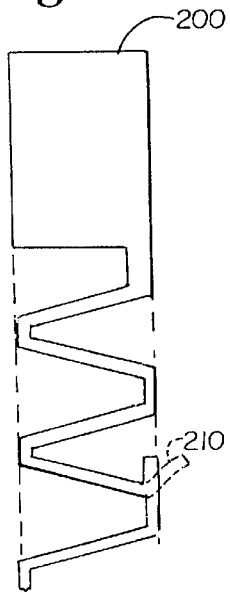
FIG. 3C shows a plan view of an alternative wavelike formation of the material in FIG. 3.
Figure 3D:
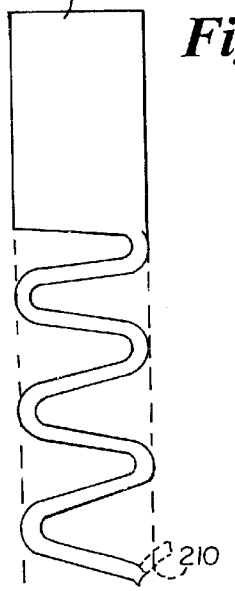
FIG. 3D shows a plan view of an alternative wavelike formation of the material of FIG. 3.
Figure 3E:
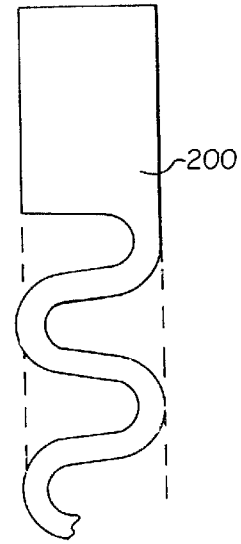
FIG. 3E shows a plan view of an alternative wavelike formation of the material of FIG. 3 having a nonuniform cross-section.

As further shown in FIG. 3A, a plurality of spaced-apart, lateral cuts 204 are made in ribbon 200. Preferably, cuts 204 extend alternately from opposed longitudinal sides 200c and 200d. Referring to FIG. 3B, the cut ribbon is then stretched from the configuration shown in FIG. 3A by applying an opposable longitudinal pulling force on the ribbon at transverse edges 200a and 200b, indicated by arrows A and B. Upon expansion, an undulating wave-like pattern 206 is produced wherein each wave has an amplitude a that corresponds to the width of ribbon 200. The period P of each wave corresponds to period P of stent segment 100 from which each strut 112 is formed.

In one preferred method of manufacture particularly applicable to a thin-walled ribbon, cuts 204 may be formed by a laser. However, other flat sheet techniques such as chemical etching or electrical discharge machining (EDM) may be employed to form cuts 204. Generally, these processes can be performed on a flat ribbon faster and with higher quality than is possible on workpieces having tubular configuration, such as noted previously with respect to the prior art device of FIG. 1. Cutting of a flat ribbon results in stents having fewer burrs and misaligned cuts over those found in stents formed from material which was cut in its tubular configuration.

Each cut 204 extends a predetermined distance across the width of ribbon 200, wherein such distance is dictated by the desired geometry of the wave produced by the cuts. Although a square wave pattern is shown in FIG. 3B, cuts 204 may produce different undulating patterns, such as an angular wave pattern shown in FIG. 3C, a serpentine pattern shown in FIG. 3D and a non-uniform, undulating pattern shown in FIG. 3E. The selection of wave geometry is dependent upon numerous factors, such as the duration of implantation and the geometry of the vascular section within which implantation occurs. Thus, the wavelike configuration resulting from such open cuts is not limited to the types shown herein.

Figure 2B:
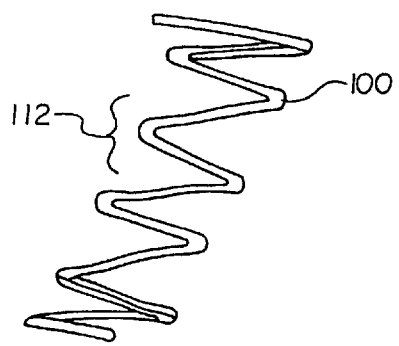
FIG. 2B shows a perspective view of a stretched and radially expanded stent of FIG. 2.

After cutting and stretching is complete, ribbon 200 is then formed into the tubular shape shown in FIG. 2B by rolling the pattern so as to bring transverse edges 200a and 200b together. The edges may then be joined by welding or the like, forming tubular stent segment 100.

Although stent 100 of FIG. 2 can be used in certain applications where limited support of a vascular section is desired, as mentioned above it may be advantageous to provide an elongated stent for longer and more tortuous vascular regions. In order to form such an elongated stent, plural stent segments 100 are arranged in spaced longitudinal succession. The spaced-apart stent segments are interconnected by connectors 114. Each connector 114 enables connection of adjacent stent segments 100 at tangential opposing endpoints corresponding to offset struts 112a and 112b. Thus, upon making cuts 204 in ribbon 200, a connector 114 can be fabricated from an extension 210 (depicted by the broken line in FIG. 3B). Connector 114 can be formed therefrom by bending and heat setting extension 210 into a position protruding outward from the pattern 206. An extension can be similarly fabricated for various wave configurations, as depicted in broken lines in FIGS. 3C and 3D.

Figure 4:
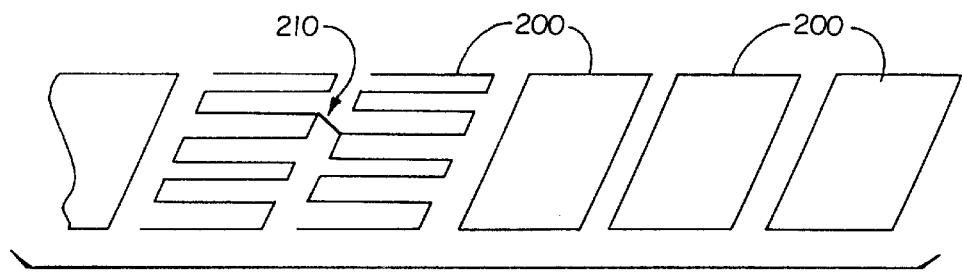
FIG. 4 shows a plan view of a multiple stent segments formed from planar sheets of stent material and having a connector affixed therebetween.

An elongate stent 100' of the type shown in FIG. 2A can now be formed in accordance with a method of the present invention. Referring initially to FIG. 4, multiple sheets 200 can be used to form the plural expandable stent segment of FIG. 2A. First, a select number of sheets 200 are formed into undulating stent patterns as shown, which patterns can be any of the sinusoidal or other geometrical patterns described hereinbefore. At least one extension 210 is fabricated from each stent pattern to produce a corresponding connector 114 that enables attachment of successively aligned stents. Thus, as depicted in FIG. 2A, a plurality of connectors 114 facilitate attachment of adjacent stent segments 100 in longitudinal succession by welding or otherwise affixing a connector from one strut 112a to an adjacent offset strut 112b. Struts 112a and 112b are interconnected at opposing strut end portions 112a' and 112b'.

Strut end portions 112a' and 112b' as shown are generally elliptical but may be rounded, square, pointed or the like. Any configuration of end portions may be employed so long as it provides an undulating pattern, as shown. When the flat form 200 (FIG. 3C) is formed into an unexpanded tube, the segments are cylindrical but the strut end portions 112a' and 112b' of adjacent stent segments remain in an opposed position relative to each other.

Positioning of connectors 114 so as to interconnect adjacent stent segments 100 is depicted in such a manner that there are three or more struts 112 between points of connection from one side of each segment to its other side. Additionally, the connectors extend angularly from a connecting end portion of one stent segment to a connecting end portion of an adjacent stent segment so as to achieve tangential intersection with corresponding parallel struts 112. Upon expansion of the stent, the adjacent stent segments are displaced relative to each other about the periphery of the stent body to accommodate flexing of the stent within paired struts without interference between adjacent stent segments, rather than by means of articulating flexible connectors between segments. Although this particular connector spacing is shown, it is understood that the connector may placed in a different configuration relative to the number of struts present within any given stent segment. The comparative number of connectors to struts can vary, depending upon the end use of the stent and its performance requirements in a vascular conduit.

Connectors 114 extend from strut end portion 112a' of stent segment 100 to another strut end portion 112b' of an adjacent stent segment 100a, which is not directly longitudinally adjacent. Rather, the angular orientation of connectors 114 interconnects radially staggered end portions. There are at least three struts 112 included between the points on each side of a stent segment 100 at which a connector 114 contacts a corresponding end portion 112a' or 112b'. This results in the connectors 114 extending in an angular direction between stent portions around the periphery of the tubular stent.

Connectors 114 are preferably of the same length, but may vary from one stent segment to another. Also, the diagonal direction may be reversed from one stent segment to another, extending upwardly in one case and downwardly in another, although all connectors between any pair of stent segments are substantially parallel. As shown in FIG. 2A, for example, the connectors 114 extend downwardly, right to left. As a result of this angular extension between adjacent stent portions, the closest adjacent end portions 112a' and 112b' between stent segments 100 and 100a are displaced from each other upon expansion of the stent as seen in FIG. 2A. The end portions are no longer opposite one another, thereby minimizing the possibility of binding or overlapping between segments (i.e., pinching, kinking).

Struts 112 are distributed in a helical fashion wherein a specific pattern of connection between stent portions is implemented. The configuration of struts to connectors results in an improved stent having a more uniform structure wherein joined regions experience lower magnitudes of force and there is less kinking in the elongated stent device. Such properties make the stent more desirable both for compression within a catheter and also during implantation within a vessel.

Figure 5:
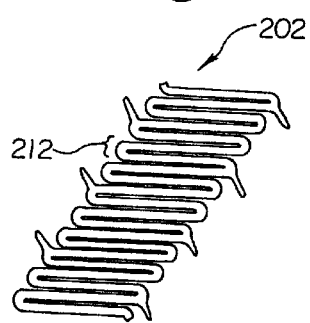
FIG. 5 shows a plan view of a stent segment formed from the material of FIG. 3 having connectors of one-half width.
Figure 6:
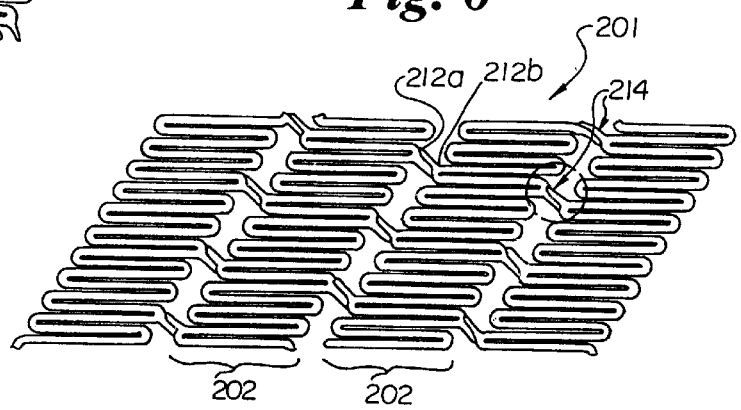
FIG. 6 shows a plan view of an elongated stent utilizing plural expandable stent segments of FIG. 5.
Figure 7:
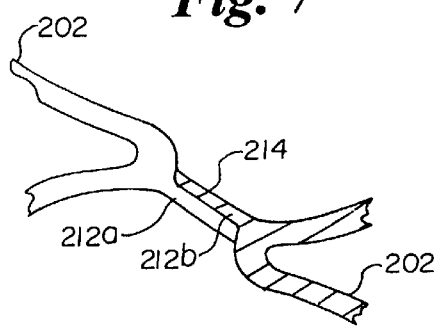
FIG. 7 shows an exploded view of a joint region at which stent segments of FIG. 5 are affixed.

In an alternative preferred embodiment shown in FIGS. 5 and 6, an extended stent 201 is formed from a plurality of adjacent stent segments 202 which are affixed to one another at a plurality of connection regions 214. Each connection region 214 comprises a pair of interconnecting elements 212a and 212b, wherein each of interconnecting elements 212a and 212b is one-half the width of a connector 114 as shown in FIG. 2A. The relationship between connectors 212a and 212b can be more easily seen in the enlarged view shown in FIG. 7, which represents a connection region 214 as circled in FIG. 6.

As described hereinabove, after formation of stent segments 202 into their respective cylindrical configurations, connectors 212a and 212b are attached to one another by welding or other appropriate means. The width of each connector 212a and 212b is one-half that of a connector 114, permitting the length of stent 201 to be easily varied.

Connectors 212a and 212b extend substantially lengthwise with respect to one another so as to promote flexibility in the connection regions 214 and in the stents themselves. Although flexibility is maintained, when stent 201 is radially expanded, the present configuration also ensures radial strength and prevents kinking between adjacent stent segments. The present invention configuration thereby enables the extended stent to bend through tortuous portions of a blood vessel into which it is inserted and simultaneously maintain the patency of that vessel over an extended period of time.

Interconnecting elements 212a and 212b can be fabricated from an extension 210 which is formed from the undulating wave-like pattern shown in FIGS. 3A–3E. As the present process for stent manufacture already discloses formation of a connector from the cut ribbon 200, it is easy to cut the width of connecting portion 210 so that the resulting interconnecting elements 212a and 212b have one-half the width of the original portion. Thus, formation of the half-width interconnection elements would not require additional cost or extensive effort to complete, resulting in a stent which is easier and cheaper to manufacture.

While the present invention is designed to provide an improved method of manufacturing a spiral wound stent, it is contemplated that such a method can be used with conventional tubular style stents, as well. Thus, the present invention shows a method of fabricating longer radius-style stents by combining multiple stents. This technique can be used on any style of stent where overlapping struts or connectors can be combined.

Various changes and modifications can be made to the present invention. It is intended that all such changes and modifications come within the scope of the invention as set forth in the following claims.

What is claimed is:

1. An expandable tubular stent, comprising:
   a first stent segment and a second stent segment spaced apart from the first segment, each of the stent segments disposed about a common longitudinal axis, each of the sent segments having a plurality of interconnected struts, the first stent segment having at least one first stent segment connection member extending from the first stent segment toward the second stent segment at an angle offset from the longitudinal axis, the second stent segment having at least one second stent segment connection member extending from the second stent segment toward the first stent segment at an angle offset from the longitudinal axis, the at least one first stent segment connection member and the at least one second stent segment connection member positioned immediately adjacent to one another in a continuous side by side relationship wherein only one side of the at least one first stent segment connection member is engaged to only one side of the at least one second stent segment connection member.

2. The stent of claim 1 wherein said stent is constructed from a biocompatible metal.

3. The stent of claim 2 wherein said biocompatible metal is selected from the group consisting of stainless steel, platinum, gold, and titanium.

4. The stent of claim 1 wherein said stent is constructed from a temperature-sensitive memory alloy.

5. The stent of claim 4 wherein said alloy is Nitinol.

6. The stent of claim 1 wherein the plurality of interconnected struts form a sinusoidal pattern.

7. The stent of claim 1 wherein the plurality of interconnected struts form a square-wave pattern.

8. The stent of claim 1 wherein three or more struts are positioned between said at least one first stent segment connection member and the at least one second stent segment connection member.

9. The stent of claim 1 wherein said plural stents are joined in longitudinal succession along the longitudinal axis.

10. The stent of claim 1 wherein said struts are distributed in a helical fashion.

11. The stent of claim 1 wherein the at least one first stent segment connection member and the at least one second stent segment connection member in combination form a connector, the at least one first stunt segment connection member and the at least one second stent segment connection member each defining one-half the width of said connector.

12. The stent of claim 1 wherein the at least one first stent segment connection member and the at least one second stent segment connection member are joined by welding.

13. An expandable tubular stent, comprising:
    a first stent segment and a second stent segment spaced apart from the first segment, each of the stent segments helically disposed about a common longitudinal axis, each of the stent segments having a plurality of interconnected struts, the first stent segment having at least one first stent segment connection member extending from the first stent segment toward the second stent segment at an angle offset from the longitudinal axis, the second stent segment having at least one second stent segment connection member extending from the second stent segment toward the first stent segment at an angle offset from the longitudinal axis, the at least one first stent segment connection member and the at least one second stent segment connection member positioned immediately adjacent to one another in a continuous side by side relationship wherein only one side of the at least one first stent segment connection member is engaged to at least one side of the only one second stent segment connection member.

14. The stent of claim 13 wherein said stent is constructed from a biocompatible metal.

15. The stent of claim 14 wherein said biocompatible metal is selected from the group consisting of stainless steel, platinum, gold, and titanium.

16. The stent of claim 13 wherein said stent is constructed from a temperature-sensitive memory alloy.

17. The stent of claim 16 wherein said alloy is Nitinol.

18. The stent of claim 13 wherein the plurality of interconnected struts form a sinusoidal pattern.

19. The stent of claim 13 wherein the plurality of interconnected struts form a square-wave pattern.

20. The stent of claim 13 wherein three or more struts are positioned between the at least one first stent segment connection member and the at least one second stent segment connection member.

21. The stent of claim 13 wherein said plural stents are joined in longitudinal succession along the longitudinal axis.

22. The stent of claim 13 wherein said struts are distributed in a helical fashion.

23. The stent of claim 13 wherein the at least one first stent segment connection member and the at least one second stent segment connection member in combination form a connector, the at least one first stent segment connection member and the at least one second stent segment connection member each defining one-half the width of said connector.

24. The stent of claim 13 wherein the at least one first stent segment connection member and the at least one second stent segment connection member are joined by welding.

25. An expandable tabular stent, comprising:

a plurality of stent segments, each of the plurality of stent segments having a plurality of interconnected struts, at least one distal connection member extending from a distal region of the interconnected struts at an angle offset from a longitudinal axis of the stent and at least one proximal connection member extending from a proximal region of the interconnected struts at an angle offset from the longitudinal axis of the stent, the at least one distal connection member of one of the plurality of stent segments being engaged to the at least one proximal connection member of another of the plurality of stent segments such that the at least one distal connection member and the at least one proximal connection member are positioned immediately adjacent to one another in a continuous side by side relationship wherein only one side of the at least one distal connection member is engaged to only one side of the at least one proximal connection member.

* * * * *